US010653226B2

(12) United States Patent
Tsubouchi et al.

(10) Patent No.: US 10,653,226 B2
(45) Date of Patent: May 19, 2020

(54) AEROSOL PRODUCT FOR FORMING WARMING CREAM COMPOSITION

(71) Applicant: Toyo Aerosol Industry Co., Ltd., Tokyo (JP)

(72) Inventors: Makoto Tsubouchi, Tokyo (JP); Tomoyuki Niinomi, Tokyo (JP)

(73) Assignee: TOYO AEROSOL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 15/542,578

(22) PCT Filed: Jan. 28, 2016

(86) PCT No.: PCT/JP2016/052420
§ 371 (c)(1),
(2) Date: Jul. 10, 2017

(87) PCT Pub. No.: WO2016/121851
PCT Pub. Date: Aug. 4, 2016

(65) Prior Publication Data
US 2017/0367461 A1 Dec. 28, 2017

(30) Foreign Application Priority Data

Jan. 30, 2015 (WO) .................. PCT/JP2015/052646

(51) Int. Cl.
B65D 83/74 (2006.01)
A45D 34/04 (2006.01)
A61K 8/26 (2006.01)
A61K 8/34 (2006.01)
A61K 8/86 (2006.01)
A61K 8/04 (2006.01)
A61Q 19/10 (2006.01)
A61K 8/37 (2006.01)
B65D 83/68 (2006.01)
A61Q 19/00 (2006.01)
B65D 83/14 (2006.01)
B65D 83/20 (2006.01)
B65D 83/32 (2006.01)
B65D 83/38 (2006.01)
B65D 83/62 (2006.01)

(52) U.S. Cl.
CPC .............. A45D 34/04 (2013.01); A61K 8/046 (2013.01); A61K 8/26 (2013.01); A61K 8/342 (2013.01); A61K 8/345 (2013.01); A61K 8/37 (2013.01); A61K 8/86 (2013.01); A61Q 19/00 (2013.01); A61Q 19/007 (2013.01); A61Q 19/10 (2013.01); B65D 83/20 (2013.01); B65D 83/32 (2013.01); B65D 83/38 (2013.01); B65D 83/62 (2013.01); B65D 83/68 (2013.01); B65D 83/752 (2013.01); A45D 2200/058 (2013.01); A45D 2200/15 (2013.01); A61K 2800/242 (2013.01); A61K 2800/592 (2013.01); A61K 2800/87 (2013.01); A61K 2800/88 (2013.01)

(58) Field of Classification Search
CPC .... B65D 83/682; B65D 83/66; B65D 83/663; B65D 83/666; B65D 83/68; B65D 83/685; B65D 83/687; B65D 83/74; B65D 83/75
See application file for complete search history.

(56) References Cited

U.S. PATENT DOCUMENTS

| 3,250,680 | A | 5/1966 | Menkart et al. | |
|---|---|---|---|---|
| 2006/0054634 | A1* | 3/2006 | Mekata | B05B 11/3081 222/94 |
| 2007/0292461 | A1* | 12/2007 | Tamarkin | A61K 8/86 424/401 |

(Continued)

FOREIGN PATENT DOCUMENTS

| EP | 0187912 A2 | 7/1986 | |
| EP | 1754518 A1 * | 2/2007 | ............... A61K 8/20 |

(Continued)

OTHER PUBLICATIONS

International Search Report dated Apr. 12, 2016 for PCT/JP2016/052420.

(Continued)

Primary Examiner — Micah Paul Young
(74) Attorney, Agent, or Firm — Lucas & Mercanti, LLP

(57) ABSTRACT

An object of the present invention is to provide an aerosol product for forming a warming cream composition which is capable of achieving excellent dispersion stability of hydration exothermic substance powder and of easily forming a warming cream composition having a sufficient warming effect. The aerosol product of the present invention includes a double structure container provided with a discharging mechanism for simultaneously discharging contents filled in the two liquid concentrate filling spaces. The propellant filling space is filled with a propellant composed of compressed gas. The first liquid concentrate filling space is filled with a composition, which includes hydration exothermic substance powder dispersed in a liquid medium containing a polyhydric alcohol and a higher alcohol and having a viscosity (at 20° C.) of 1000 to 10000 mPa·s, containing 10 to 40% by mass of the hydration exothermic substance powder, and 0.05 to 20% by mass of the higher alcohol, and having a viscosity (at 20° C.) of 1000 to 125000 mPa·s. The second liquid concentrate filling space is filled with a composition containing water and 0.1 to 10% by mass of a viscosity modifier.

11 Claims, 3 Drawing Sheets

(56) References Cited

U.S. PATENT DOCUMENTS

| 2012/0014885 A1* | 1/2012 | Collier | A61Q 7/02 |
| | | | 424/59 |
| 2014/0246515 A1* | 9/2014 | Nakajima | B65D 83/682 |
| | | | 239/307 |

FOREIGN PATENT DOCUMENTS

| EP | 1754518 A1 | 2/2007 |
| GB | 1248536 A1 | 10/1971 |
| JP | 3-123732 A | 5/1991 |
| JP | 4-89424 A | 3/1992 |
| JP | 4-187628 A | 7/1992 |
| JP | 10-306276 A | 11/1998 |
| JP | 2002-047136 A | 2/2002 |
| JP | 2004-161292 A | 6/2004 |
| JP | 2004-250440 A | 9/2004 |
| JP | 2005-075917 A | 3/2005 |
| JP | 3882685 B | 11/2006 |
| WO | 2009-130246 A1 | 10/2009 |
| WO | 2014-027410 A1 | 2/2014 |

OTHER PUBLICATIONS

Extended European Search Report dated Oct. 25, 2017 from the corresponding European Application No. PCT/JP2016052420.

* cited by examiner

AEROSOL PRODUCT FOR FORMING WARMING CREAM COMPOSITION

CROSS REFERENCE TO RELATED APPLICATION

This Application is a 371 of PCT/JP2016/052420 filed on Jan. 28, 2016 which, in turn, claimed the priority of Japanese PCT Patent Application No. PCT/JP2015/052646 filed Jan. 30, 2015, both applications are incorporated herein by reference.

TECHNICAL FIELD

The present invention relates to an aerosol product for forming a warming cream composition.

BACKGROUND ART

Conventionally, various compositions have been proposed as a composition using a hydration exothermic substance, such as zeolite, which generates heat through a chemical reaction or a physical-chemical reaction when it is brought into contact with water (see, for example, Patent Literatures 1 to 3).

However, in a composition containing hydration exothermic substance powder (hereinafter, also referred to as a "hydration exothermic substance-containing composition"), a sufficient warming effect cannot be stably exhibited since the hydration exothermic substance powder is likely to be precipitated during storage and to be hard to redispense easily.

Thus, with regards to hydration exothermic substance-containing compositions, attempts have been made to improve the dispersion stability or the redispersibility of the hydration exothermic substance powder by, for example, blending thickeners, clay minerals, surfactants, or the like (see, for example, Patent Literatures 4 to 6).

However, the hydration exothermic substance-containing composition in which thickeners, clay minerals or surfactants are blended is problematic in that the increase in their blending amount may cause a sticky, or frictional feeling after use, particularly for human body applications, and thus, a favorable sense of use cannot be obtained. Such problems are prominent when water-soluble polymer thickeners and clay minerals are blended, since they have adhesiveness.

Furthermore, with regards to the hydration exothermic substance-containing composition, in order to obtain a warming effect, it is necessary to bring water into contact with the hydration exothermic substance powder within the hydration exothermic substance-containing composition. Therefore, upon application of a hydration exothermic substance-containing composition, the user may have to mix the hydration exothermic substance-containing composition with water. In such a case, it may not be possible for the user to mix them in an appropriate mixing ratio, and as a result, a sufficient warming effect may not be exhibited.

Then, from the viewpoint of convenience, it is proposed that the hydration exothermic substance-containing composition is produced as an aerosol product (see, for example, Patent Literature 1). Specifically, it is proposed that the hydration exothermic substance-containing composition and a water-containing composition are filled into a two-liquid mixing type aerosol container in a state where they are separated from each other.

However, in such an aerosol product, since the hydration exothermic substance-containing composition and the water-containing composition are discharged along with a propellant, due to heat of vaporization of the propellant at the application site, particularly for human body applications, so that a sufficient warming effect cannot be achieved.

CITATION LIST

Patent Literature

Patent Literature 1: Japanese Patent Application Laid-open Publication No. H4-89424
Patent Literature 2: European Patent No. 187912
Patent Literature 3: U.S. Pat. No. 3,250,680
Patent Literature 4: Japanese Patent Application Laid-open Publication No. H3-123732
Patent Literature 5: Japanese Patent Application Laid-open Publication No. H4-187628
Patent Literature 6: Japanese Patent No. 3882685

SUMMARY OF THE INVENTION

Technical Problem

The present invention has been made under the above-mentioned circumstances, and an object of the present invention is to provide an aerosol product or an aerosol dispenser for forming a warming cream composition which is capable of achieving excellent dispersion stability of the hydration exothermic substance powder and of easily forming a warming cream composition having a sufficient warming effect.

Solution to Problem

An aerosol product for forming a warming cream composition of the present invention includes a double structure container including a propellant filling space, two independent liquid concentrate filling spaces, and a discharging mechanism for simultaneously discharging contents filled in the two liquid concentrate filling spaces. The propellant filling space in the double structure container is filled with a propellant composed of compressed gas; the first liquid concentrate filling space in the double structure container is filled with a first liquid concentrate composition, and the second liquid concentrate filling space in the double structure container is filled with a second liquid concentrate composition; the first liquid concentrate composition includes hydration exothermic substance powder dispersed in a liquid medium containing a polyhydric alcohol and a higher alcohol and having a viscosity of 1000 to 10000 mPa·s at a temperature of 20° C., wherein a content rate of the hydration exothermic substance powder is 10 to 40% by mass, and the content rate of the higher alcohol is 0.05 to 20% by mass, and the viscosity is 1000 to 125000 mPa·s at a temperature of 20° C.; the second liquid concentrate composition contains water and a viscosity modifier, wherein the content rate of the viscosity modifier is 0.1 to 10% by mass; and the first liquid concentrate composition discharged from the first liquid concentrate filling space and the second liquid concentrate composition discharged from the second liquid concentrate filling space are mixed with each other to form a warming cream composition.

In the aerosol product for forming a warming cream composition of the present invention, it is preferable that the mixture ratio of the first liquid concentrate composition discharged from the first liquid concentrate filling space and the second liquid concentrate composition discharged from the second liquid concentrate filling space (mass of the first liquid concentrate composition:mass of the second liquid concentrate composition) is 0.8:1.2 to 1.2:0.8.

In the aerosol product for forming a warming cream composition of the present invention, it is preferable that the first liquid concentrate composition has a viscosity of 1000 to 125000 mPa·s at a temperature of 20° C., and the second liquid concentrate composition has a viscosity of 1000 to 125000 mPa·s at a temperature of 20° C.

It is preferable that the aerosol product for forming a warming cream composition of the present invention is to be used for the human body.

Advantageous Effect of Invention

An aerosol product for forming a warming cream composition of the present invention includes a double structure container provided with a discharging mechanism for simultaneously discharging contents filled in the two liquid concentrate filling spaces. One of the two liquid concentrate filling spaces is filled with a first liquid concentrate composition having a specific viscosity in which hydration exothermic substance powder is dispersed in a specific rate within a liquid medium containing a higher alcohol in a specific rate and having a specific viscosity. The other liquid concentrate filling space is filled with a second liquid concentrate composition containing a viscosity modifier in a specific rate. Consequently, the first liquid concentrate composition is in a state where the hydration exothermic substance powder is always homogeneously dispersed in the liquid medium. Therefore, when the first liquid concentrate composition is mixed with the second liquid concentrate composition, the homogeneously existing hydration exothermic substance powder evenly exhibits an appropriate exothermic effect. Furthermore, since the first liquid concentrate composition and the second liquid concentrate composition can be discharged simultaneously in an appropriate amount from each of the liquid concentrate filling spaces in the double structure container, the first liquid concentrate composition and the second liquid concentrate composition can be always mixed with each other at a constant ratio. The discharged amount of one of the liquid concentrate compositions is not excessively larger as compared with the discharged amount of the other liquid concentrate composition. Furthermore, since a propellant is not discharged from the double structure container along with the first and second liquid concentrate compositions, a cooling sensation due to vaporization of the propellant does not occur at the application site.

Therefore, the aerosol product for forming a warming cream composition of the present invention makes it possible to easily form a warming cream composition that can achieve excellent dispersion stability of the hydration exothermic substance powder and have a sufficient warming effect.

DESCRIPTION OF EMBODIMENTS

Figure 1:
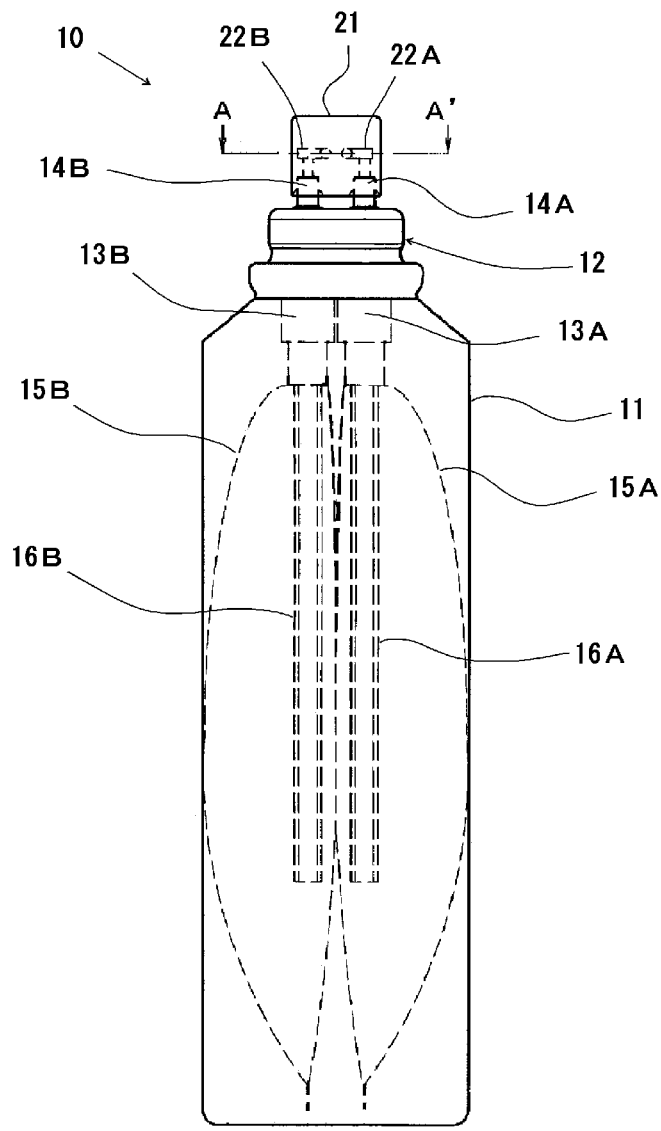
FIG. 1 is an illustration of one example of a configuration of a double structure container used in an aerosol product for forming a warming cream composition of the present invention.

The aerosol product for forming a warming cream composition of the present invention includes a double structure container including a propellant filling space and two individual liquid concentrate filling spaces, and being provided with a discharging mechanism for simultaneously discharging the contents filled in the two liquid concentrate filling spaces. In this double structure container, the propellant filling space is filled with a propellant composed of compressed gas, while the first liquid concentrate filling space is filled with a first liquid concentrate composition containing hydration exothermic substance powder, and the second liquid concentrate filling space is filled with a second liquid concentrate composition containing water.

In the aerosol product for forming a warming cream composition of the present invention, the first liquid concentrate composition and the second liquid concentrate composition simultaneously discharged from the first liquid concentrate filling space and the second liquid concentrate filling space, respectively, are mixed with each other to form a warming cream composition. In the warming cream composition, the hydration exothermic substance powder and water react with each other. The reaction exhibits an exothermic effect in the hydration exothermic substance powder, with which a warming effect is achieved.

First Liquid Concentrate Composition

The first liquid concentrate composition substantially does not contain water, and is obtained by dispersing hydration exothermic substance powder in a liquid medium containing a polyhydric alcohol and a higher alcohol.

In this first liquid concentrate composition, the hydration exothermic substance powder, the polyhydric alcohol and the higher alcohol are essential components. The content rate of the hydration exothermic substance powder is 10 to 40% by mass, and the content rate of the higher alcohol is 0.05 to 20% by mass.

In the first liquid concentrate composition, the liquid medium is miscible to water, and is required to have a viscosity of 1000 to 10000 mPa·s, and preferably 1000 to 5000 mPa·s, at a temperature of 20° C.

When the viscosity of the liquid medium is within the above-mentioned range, the hydration exothermic substance powder has sufficient dispersion stability in the first liquid concentrate composition obtained by blending the hydration exothermic substance powder into the liquid medium.

On the other hand, excessively high viscosity of the liquid medium may cause for the discharge difficult.

Furthermore, excessively low viscosity of the liquid medium causes to unstabilize the dispersion state of the hydration exothermic substance powder in the first liquid concentrate composition, and may make it difficult to obtain a sufficient dispersion state at the time of use.

In the first liquid concentrate composition, polyhydric alcohol is a main component of the liquid medium.

Specific examples of the polyhydric alcohol to be used in the first liquid concentrate composition include those which are liquid at ordinary temperature (at 20° C.), such as propylene glycol, 1,3-butylene glycol, polyethylene glycol, glycerine, and polyglycerin. These may be used singly or in combination of two or more of them.

Among them, polyethylene glycol is preferable since the warming cream composition to be formed can exhibit a sufficient warming effect. Furthermore, as the polyethylene glycol, polyethylene glycol having an average molecular weight of 400 or less is preferable. When polyethylene glycol having an average molecular weight of 400 or less is used as the polyhydric alcohol, the warming cream composition to be formed has a better warming effect, since the polyethylene glycol is liquid and is not solidified at low temperature and has high heat of dissolution.

The content rate of the polyhydric alcohol is preferably 40% by mass or more with respect to 100% by mass of the first liquid concentrate composition, in view of the relation with content rates of the other constituting components.

In the first liquid concentrate composition, the higher alcohol is necessary component for achieving dispersion stability of the hydration exothermic substance powder. Furthermore, it is used as an agent for improving the sense of use, and the like, particularly for human body applications. Furthermore, this higher alcohol is in a state where it is dispersed or emulsified in the polyhydric alcohol.

Specific examples of the higher alcohol to be used for this first liquid concentrate composition include cetyl alcohol, lauryl alcohol, myristyl alcohol, cetostearyl alcohol, arachyl alcohol, behenyl alcohol, oleyl alcohol, jojoba alcohol, stearyl alcohol, octyldodecanol, hexyldecanol, isostearyl alcohol, and the like. These may be used singly or in combination of two or more of them. Among them, alcohol having 16 or more carbon atoms is preferable, since a higher alcohol having a larger molecular weight can achieve a high viscosity-improving effect with a smaller blending amount. Specifically, cetyl alcohol, cetostearyl alcohol, arachyl alcohol, behenyl alcohol, oleyl alcohol, stearyl alcohol, octyldodecanol, hexyldecanol and isostearyl alcohol are preferable.

The content rate of the higher alcohol needs to be 0.05 to 20% by mass, preferably 0.05 to 10% by mass, and further preferably 0.05 to 8% by mass, with respect to 100% by mass of the first liquid concentrate composition.

When the content rate of the higher alcohol is too high, the viscosity of the liquid medium and the viscosity of the first liquid concentrate composition are increased. Accordingly, a large difference occurs between the discharge amount of the first liquid concentrate composition and the discharge amount of the second liquid concentrate composition. As a result, the first liquid concentrate composition and the second liquid concentrate composition are not sufficiently mixed with each other, and the formed warming cream composition may not have a sufficient warming effect.

On the other hand, when the content rate of the higher alcohol is too low, the viscosity of the liquid medium and the viscosity of the first liquid concentrate composition become low. Accordingly, in the first liquid concentrate composition, a dispersion state of the hydration exothermic substance powder becomes instable, and it may be difficult to obtain a sufficient dispersion state at the time of use. Furthermore, particularly for human body applications, a sticky feeling or the like may occur, and thus a favorable sense of use may not be obtained.

The hydration exothermic substance powder as the essential component of the first liquid concentrate composition is powder of a substance that causes a chemical reaction or a physical-chemical reaction so as to generate heat when it is brought into contact with water.

Specific examples of the hydration exothermic substance to be used for the first liquid concentrate composition include inorganic salts such as zeolite, calcium chloride, magnesium chloride, magnesium sulfate, sodium carbonate and silicic anhydride. These may be used singly or in combination of two or more of them. Among them, zeolite, silicic anhydride, sodium carbonate or mixtures thereof are preferable.

Furthermore, the hydration exothermic substance powder is present as dispersed particles in the first liquid concentrate composition, and the average particle diameter, that is to say the average particle diameter of the hydration exothermic substance powder (dispersed particles), is preferably 50 µm or less, and more preferably 20 µm or less.

When the average particle diameter of the hydration exothermic substance powder is too large, clogging may occur in the aerosol valve. Furthermore, particularly when the aerosol product for forming a warming cream composition is applied to the skin surface of a human body, the discharged product may cause a rough feeling at the application site.

When the average particle diameter of the hydration exothermic substance powder (dispersed particles) is 20 µm or less, occurrence of clogging in the aerosol valve can be prevented, and high dispersion stability of the hydration exothermic substance powder is achieved. Furthermore, since the specific surface area of the hydration exothermic substance powder becomes larger, the warming cream composition can exhibit a sufficient warming effect even with a small amount of mixture. Furthermore, the speed at which the exothermic effect by the hydration exothermic substance powder is exhibited, that is the reaction speed between the hydration exothermic substance powder and water, is increased. Furthermore, when it is applied to the skin surface for a human body, the sense of use (specifically, the feeling of smoothness) is improved.

The content rate of the hydration exothermic substance powder needs to be 10 to 40% by mass and preferably 20 to 30% by mass with respect to 100% by mass of the first liquid concentrate composition.

When the content rate of the hydration exothermic substance powder is too high, clogging may occur in the aerosol valve, the viscosity of the first liquid concentrate composition becomes excessively high, and accordingly, a large difference occurs between the discharge amount of the first liquid concentrate composition and the discharge amount of the second liquid concentrate composition. As a result, the first liquid concentrate composition and the second liquid concentrate composition may not be sufficiently mixed with each other, and the warming cream composition to be formed may not exhibit a sufficient warming effect. Furthermore, when the first liquid concentrate composition and the second liquid concentrate composition are mixed with each other, the temperature of the mixture may become temporarily high, leading to burns at the application site in cases of human body applications. That is to say, when the aerosol product for forming a warming cream composition is applied for human body, sufficient safety during its use may not be achieved.

On the other hand, when the content rate of the hydration exothermic substance powder is too low, the formed warming cream composition may not be able to have a sufficient warming effect.

The first liquid concentrate composition may contain optional components if necessary, in addition to the essential components (specifically, the hydration exothermic substance powder, polyhydric alcohol, and higher alcohol). Specifically, the liquid medium may contain optional components.

Examples of the optional components include perfume, a surfactant, esters, waxes, and the like in addition to components constituting toiletry products such as cosmetic materials, active ingredients of medicine, and the like, which are considered as necessary depending upon the purpose of use of the aerosol product for forming a warming cream composition. Among them, surfactants and esters are preferable.

In the first liquid concentrate composition, the surfactant has a function of an emulsifying agent for the liquid medium, and the like.

In the first liquid concentrate composition, an anionic surfactant or a nonionic surfactant having an HLB value of 6 to 13 are suitably used as the surfactant.

Use of the anionic surfactant or nonionic surfactant having an HLB value of 6 to 13 as the surfactant can allow the higher alcohol homogeneously dispersed in the polyhydric alcohol in the liquid medium so as to form a favorable emulsified state.

Specific examples of the anionic surfactant to be suitably used for the first liquid concentrate composition include sodium cetylsulfate, sodium lauryl sulfoacetate, and the like.

Specific examples of the nonionic surfactant to be suitably used for the first liquid concentrate composition include polyglyceryl-6 oleate (HLB value: 9.0), Ceteth-2 (HLB value: 8.0), and PEG-20 hydrogenated castor oil (HLB value: 10.5), and the like.

The content rate of the surfactant is different depending on the types of the surfactants, the purposes of use of the aerosol product for forming a warming cream composition, the types and the content rates of other constituent components of the first liquid concentrate composition, and the like, but is preferably 0.05 to 5% by mass with respect to 100% by mass of the first liquid concentrate composition.

In the first liquid concentrate composition, esters act as, for example, an agent for adjusting a viscosity of the first liquid concentrate composition, and, particularly for human body applications, an agent for improving the sense of use, such as a moisturizing agent or an emollient agent.

Examples of esters to be used for the first liquid concentrate composition include higher fatty acid esters such as ethyl linoleate, isopropyl myristate, isopropyl palmitate, isopropyl isostearate, lanolin fatty acid isopropyl ester, hexyl lanolate, myristyl myristate, cetyl lactate, octyldodecyl myristate, decyl oleate, octyldodecyl oleate, cetyl octanoate, dioctyl succinate, glyceryl tricaprylate, glyceryl triisostearate, propylene glycol dicaprylate, ethyl oleate, cetyl palmitate and glyceryl tri(caprylate/caprate). These may be used singly or in combination of two or more of them.

The content rate of esters may differ depending on the purpose of use of the aerosol product for forming a warming cream composition, or the types and the content rates of other constituent components of the first liquid concentrate composition. However, the content rate is preferably 0.03 to 5% by mass with respect to 100% by mass of the first liquid concentrate composition.

When the content rate of the esters is too high, particularly for human body applications, a sticky feeling may occur, and the product may not sufficiently provide a favorable sense of use.

On the other hand, when the content rate of the esters is too low, the effects of esters in the aerosol product for forming a warming cream composition may not be sufficiently achieved.

The first liquid concentrate composition composed of the essential and optional components as described above needs to have a viscosity of 1000 to 125000 mPa·s, preferably 1000 to 50000 mPa·s, and furthermore preferably 10000 to 25000 mPa·s, at a temperature of 20° C.

Excessively high viscosity of the first liquid concentrate composition makes the discharge difficult. Furthermore, the expected discharge amount relative to the discharge amount of the second liquid concentrate composition may not be obtained.

On the other hand, excessively low viscosity of the first liquid concentrate composition may lead to dripping at the application site. Furthermore, a favorable sense of use may not be obtained.

Furthermore, the viscosity of the first liquid concentrate composition at a temperature of 20° C. is preferably lower than the viscosity of the below-mentioned second liquid concentrate composition at a temperature of 20° C.

When the viscosity of the first liquid concentrate composition is higher than that of the second liquid concentrate composition, the discharge property of the first liquid concentrate composition becomes very small as compared with that of the second liquid concentrate composition due to the fact that it contains powder (specifically, hydration exothermic substance powder). Consequently, the discharge amount of the first liquid concentrate composition discharged from the first liquid concentrate filling space becomes too small as compared with the discharge amount of the second liquid concentrate composition discharged from the second liquid concentrate filling space, which may make it difficult for the warming cream composition to exhibit a sufficient warming effect.

Second Liquid Concentrate Composition

The second liquid concentrate composition contains water and a viscosity modifier as essential components. The content rate of the viscosity modifier is 0.1 to 10% by mass.

Water as the essential component of the second liquid concentrate composition may be purified water or ion-exchanged water.

The content rate of water is preferably 90.0 to 99.9% by mass with respect to 100% by mass of the second liquid concentrate composition.

When the content rate of water is too high, the viscosity modifier may not be contained in a sufficient rate.

On the other hand, when the content rate of water is too low, the warming cream composition may not exhibit a sufficient warming effect.

Examples of the viscosity modifier, as the essential component of the second liquid concentrate composition, include thickener such as cellulose derivative, xanthan gum and a carboxyvinyl polymer, and others.

These may be used singly or in combination of two or more of them.

The content rate of the viscosity modifier needs to be 0.1 to 10% by mass and preferably 0.2 to 5% by mass, with respect to 100% by mass of the second liquid concentrate composition.

When the content rate of the viscosity modifier is in the above-mentioned range, even when a thickener is used as the viscosity modifier, the content rate of the thickener in the discharged product (a warming cream composition) of the aerosol product for forming a warming cream composition becomes small. Consequently, particularly for human body applications, occurrence of a sticky feeling due to containing of the thickener can be prevented or suppressed.

On the other hand, when the content rate of the viscosity modifier is too high, the content rate of water in the second liquid concentrate composition becomes smaller. Consequently, the formed warming cream composition may not exhibit a sufficient warming effect. Furthermore, particularly for human body applications, a sticky feeling may occur, so that a favorable sense of use cannot be obtained.

Furthermore, when the content rate of the viscosity modifier is too low, dripping may occur at the application site, and a large difference occurs between the discharge amount of the first liquid concentrate composition and the discharge amount of the second liquid concentrate composition, which may lead to the formed warming cream composition exhibiting an insufficient warming effect.

It is preferable that the second liquid concentrate composition contains only the essential components (specifically, water and a viscosity modifier), that is to say it does not contain optional components. However, the second liquid concentrate composition may contain optional components, if necessary. Examples of the optional components include neutralizers (neutralizers for viscosity modification), and the like.

The second liquid concentrate composition including the above-mentioned essential components and optional components has a viscosity of preferably 1000 to 125000 mPa·s, and further preferably 10000 to 125000 mPa·s, at a temperature of 20° C.

When the viscosity of the second liquid concentrate composition is too high, a large difference occurs between the discharge amount of the first liquid concentrate composition and the discharge amount of the second liquid concentrate composition. As a result, the second liquid concentrate composition may not be sufficiently mixed with the first liquid concentrate composition, so that the formed warming cream composition exhibits an insufficient warming effect.

On the other hand, when the viscosity of the second liquid concentrate composition is too low, dripping may occur at the application site. Furthermore, a large difference may occur between the discharge amount of the first liquid concentrate composition and the discharge amount of the second liquid concentrate composition, which may lead to the formed warming cream composition exhibiting an insufficient warming effect.

Furthermore, as mentioned above, the viscosity of the second liquid concentrate composition is preferably higher than the viscosity of the first liquid concentrate composition from the viewpoint of the discharge property of the first and second liquid concentrate compositions.

Propellant

Compressed gas is used as a propellant.

Examples of the compressed gas include nitrous oxide gas, nitrogen gas, carbon dioxide gas, and mixture gase thereof.

The propellant is not discharged from the propellant filling space to the outside of the double structure container along with the first liquid concentrate composition and the second liquid concentrate composition which are discharged simultaneously.

The propellant is preferably enclosed such that the pressure when it is enclosed in the double structure container is 0.3 to 1.2 MPa at 25° C.

If the filling pressure of the propellant (inner pressure of the product) is too high or too low, in both cases, the product may not be sprayed in a favorable manner.

Double Structure Container

The double structure container constituting the aerosol product for forming a warming cream composition of the present invention includes a propellant filling space to be filled with a propellant, a first liquid concentrate filling space to be filled with a first liquid concentrate composition, and a second liquid concentrate filling space to be filled with a second liquid concentrate composition. The double structure container further includes a discharging mechanism for discharging the first and second liquid concentrate compositions simultaneously from the first and second liquid concentrate filling spaces, respectively.

Specific examples of the double structure container used for the present invention include the following four containers shown in FIGS. 1 to 6.

Figure 2:
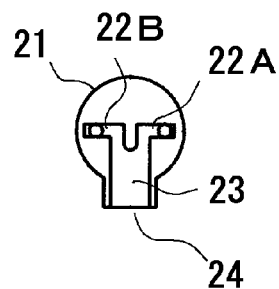
FIG. 2 is a sectional view showing an A-A' section of FIG. 1.

FIG. 1 is an illustration of one example of a configuration of a double structure container used in an aerosol product for forming a warming cream composition of the present invention, and FIG. 2 is a sectional view showing an A-A' section of FIG. 1.

This double structure container 10 includes a pressure resistant container 11 made of metal and provided with an aerosol valve 12. The inside of the pressure resistant container 11 is provided with a first inner bag 15A that is made of, for example, aluminum laminated film and defines a first liquid concentrate filling space to be filled with the first liquid concentrate composition, and a second inner bag 15B that is made of, for example, aluminum laminated film and defines a second liquid concentrate filling space to be filled with the second liquid concentrate composition. Also, inside the pressure resistant container 11, a space between the pressure resistant container 11 and each of the first inner bag 15A and the second inner bag 15B forms a propellant filling space to be filled with the propellant. Furthermore, the aerosol valve 12 is provided with a first stem 14A and a second stem 14B each having a stem passage inside and are arranged movable up and down inside a first housing 13A and a second housing 13B, respectively. A shared actuator 21 is provided on the upper ends of these first and second stems 14A and 14B.

In the example shown in the drawings, a reference symbol 16A denotes a first dip tube that communicates with the stem passage in the first stem 14A at the lower end of the first housing 13A, and extends toward the bottom of the pressure resistant container 11 inside the first inner bag 15A. A reference symbol 16B denotes a second dip tube that communicates with the stem passage in the second stem 14B at the lower end of the second housing 13B, and extends toward the bottom of the pressure resistant container 11 inside the second inner bag 15B.

In FIG. 1, the component elements disposed inside the pressure resistant container 11 and the actuator 21 are drawn with broken lines.

The shared actuator 21 is provided with a first actuator passage 22A that communicates with the stem passage of the first stem 14A, a second actuator passage 22B that communicates with the stem passage in the second stem 14B, and a discharge space 23 that communicates with these first and second actuator passages 22A and 22B at one end and forms a discharge port 24 at the other end.

In this way, the shared actuator 21 is provided on the first stem 14A of the first inner bag 15A and the second stem 14B of the second inner bag 15B so as to form the discharging mechanism for discharging the first liquid concentrate composition filled in the first inner bag 15A and the second liquid concentrate composition filled in the second inner bag 15B simultaneously from the first inner bag 15A and the second inner bag 15B, respectively.

In the double structure container 10 having such a configuration, the first inner bag 15A is filled with the first liquid concentrate composition while the second inner bag 15B is filled with the second liquid concentrate composition, and furthermore, the propellant filling space is filled with a propellant. Thus, the inside of the pressure resistant container 11 is always pressurized with the propellant. Therefore, when the actuator 21 is operated (depressed), the pressure of the propellant allows the first and second inner bags 15A and 15B to contract, and thereby the first and second liquid concentrate compositions are discharged simultaneously from the first and second inner bags 15A and 15B, respectively. Then, the first and second liquid concentrate compositions are discharged from the discharge port 24 of the actuator 21.

Specifically, in the double structure container 10 filled with the first and second liquid concentrate compositions and the propellant, when the actuator 21 is not operated to be depressed, the first and second stems 14A and 14B are pushed upward to shut off the stem passages of the first and second stems 14A and 14B from the inside of the pressure resistant container 11. On the other hand, when the actuator 21 is operated to be depressed, the first and second stems 14A and 14B are pressed down, and thereby their stem passages of the first and second stems 14A and 14B are simultaneously communicated with the inside of the pressure resistant container 11. The first liquid concentrate composition inside the first inner bag 15A and the second liquid concentrate composition inside the second inner bag 15B flow through the fluid passages formed by the first dip tube 16A and the second dip tube 16B, respectively, and are discharged simultaneously. The first and second liquid concentrate compositions thus discharged simultaneously flow through the stem passages of the first and second stems 14A and 14B and the first and second actuator passages 22A and 22B, respectively, and reach the discharge space 23. In the process of passing through the discharge space 23, the first and second liquid concentrate compositions are discharged from the discharge port 24 without being mixed with each other. Then, the first and second liquid concentrate compositions discharged from the discharge port 24 are mixed with each other by, for example, fingers of a user, at the application site, and the warming cream composition is formed.

Figure 3:
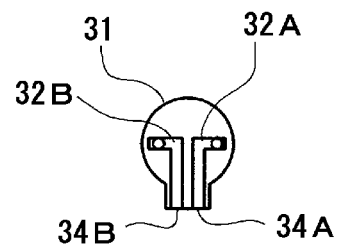
FIG. 3 is an illustration of another example of a configuration of a double structure container used in an aerosol product for forming a warming cream composition of the present invention.

FIG. 3 is an illustration of another example of a configuration of a double structure container used in an aerosol product for forming a warming cream composition of the present invention. Specifically, FIG. 3 is a sectional view for illustrating the configuration of the actuator for the double structure container.

This double structure container has the same configuration as that of the double structure container 10 shown in FIGS. 1 and 2 except that it has an actuator 31 instead of the actuator 21 of the double structure container 10 of FIGS. 1 and 2. The actuator 31 has two discharge ports (specifically, a first discharge port 34A and a second discharge port 34B) and is configured to separately discharge the first and second liquid concentrate compositions from the two respective discharge ports.

That is to say, the double structure container according to FIG. 3 includes the actuator 31, and a pressure resistant container that is configured similarly to the pressure resistant container 11 constituting the double structure container 10 shown in FIGS. 1 and 2.

The actuator 31 is configured to include a first actuator passage 32A that communicates with the stem passage of a first stem at one end and forms a first discharge port 34A at the other end, and a second actuator passage 32B that communicates with the stem passage of a second stem at one end and forms a second discharge port 34B at the other end.

The actuator 31 is shared by both of the first and second stems and provided on the upper ends of the first and second stems, similarly to the actuator 21 of the double structure container 10 shown in FIGS. 1 and 2.

In the double structure container having such a configuration, when the actuator 31 is operated to be depressed in a state where the first and second liquid concentrate compositions and the propellant are filled therein, the first liquid concentrate composition in the first inner bag and the second liquid concentrate composition in the second inner bag are simultaneously discharged. The first liquid concentrate composition is discharged from the first discharge port 34A through the stem passage in the first stem of the aerosol valve and the first actuator passage 32A, while the second liquid concentrate composition is discharged from the second discharge port 34B through the stem passage in the second stem of the aerosol valve and the second actuator passage 32B. Then, the first and second liquid concentrate compositions discharged from the first and second discharge ports 34A and 34B respectively are mixed with each other by, for example, fingers of a user, to form a warming cream composition at the application site.

Figure 4:
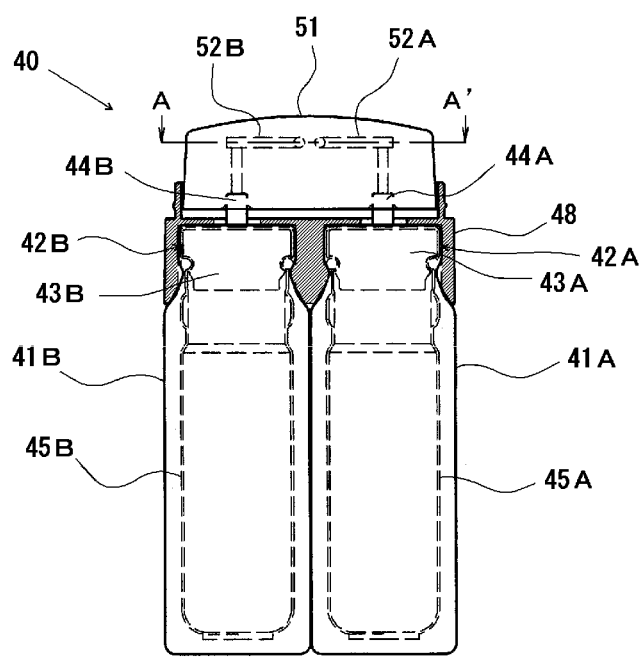
FIG. 4 is an illustration of still another example of a configuration of a double structure container used in an aerosol product for forming a warming cream composition of the present invention.
Figure 5:
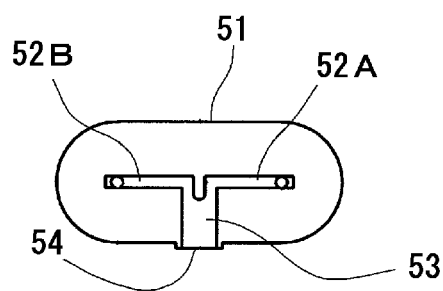
FIG. 5 is a sectional view showing an A-A' section of FIG. 4.

FIG. 4 is an illustration of still another example of a configuration of a double structure container used in an aerosol product for forming a warming cream composition of the present invention, and FIG. 5 is a sectional view showing an A-A' section of FIG. 4.

This double structure container 40 has a container main body configured to have a first pressure resistant container 41A made of metal and provided with a first aerosol valve 42A, and a second pressure resistant container 41B made of metal and provided with a second aerosol valve 42B, which are integrally formed with a container fixing member 48.

The inside of the first pressure resistant container 41A is provided with a first inner bag 45A that is made of, for example, a polyethylene sheet and defines a first liquid concentrate filling space to be filled with the first liquid concentrate composition, and a propellant filling space to be filled with the propellant, which is formed by the gap between the first pressure resistant container 41A and the first inner bag 45A. The first aerosol valve 42A is provided with a first stem 44A having a stem passage inside and is disposed movable up and down inside a first housing 43A.

On the other hand, the second pressure resistant container 41B has a similar configuration to that of the first pressure resistant container 41A. Specifically, the inside of the second pressure resistant container 41B is provided with a second inner bag 45B that is made of, for example, a polyethylene sheet, and defines a second liquid concentrate filling space to be filled with the second liquid concentrate composition, and a propellant filling space to be filled with the propellant, which is formed by the gap between the second pressure resistant container 41B and the second inner bag 45B.

The second aerosol valve 42B is provided with a second stem 44B having a stem passage inside and is disposed movable up and down inside a second housing 43B.

In the example of this drawing, the container fixing member 48 has an elliptic cylinderical outer shape, and a recess having a diameter that matches the first housing 43A, and a recess having a diameter that matches the second housing 43B are formed on one surface of the container fixing member 48 (the lower surface of the container fixing member 48 in FIG. 4). The first housing 43A and the second housing 43B are fitted in the respective recesses so that the first and second pressure resistant containers 41A and 41B are fixed. The first and second pressure resistant containers 41A and 41B are fixed to the container fixing member 48 with the first stem 44A and the second stem 44B protruding from the through holes formed in respective central parts of the bottoms of the recesses of the container fixing member 48 and having diameters that match those of the first and second stems 44A and 44B.

In FIG. 4, the constituent elements disposed inside the first pressure resistant container 41A, second pressure resistant container 41B and actuator 51 are drawn with broken lines.

A shared actuator 51 is provided on the upper ends of the first stem 44A of the first aerosol valve 42A and the second stem 44B of the second aerosol valve 42B.

The shared actuator 51 is provided with a first actuator passage 52A that communicates with the stem passage in the first stem 44A, a second actuator passage 52B that communicates with the stem passage in the second stem 44B, and a discharge space 53 that communicates with these first and second actuator passages 52A and 52B at one end and forms a discharge port 54 at the other end.

In this way, the shared actuator 51 is provided on the first stem 44A and the second stem 44B so as to form the discharging mechanism for discharging the first liquid concentrate composition filled in the first inner bag 45A and the second liquid concentrate composition filled in the second inner bag 45B simultaneously from the first inner bag 45A and the second inner bag 45B, respectively.

In the double structure container 40 having such a configuration, in the first pressure resistant container 41A, the first inner bag 45A is filled with the first liquid concentrate composition and the propellant filling space is filled with the propellant, so that the inside of the first pressure resistant container 41A is always pressurized by the propellant. In the second pressure resistant container 41B, the second inner bag 45B is filled with the second liquid concentrate composition, and the propellant filling space is filled with the propellant, so that the inside of the second pressure resistant container 41B is always pressurized by the propellant. Thus, when the actuator 51 is operated (or depressed), the pressure of the propellant allows the first and second inner bags 45A and 45B to contract, and thereby the first and second liquid concentrate compositions are discharged simultaneously from the first and second inner bags 45A and 45B, and then the first and second liquid concentrate compositions are discharged from the discharge port 54 of the actuator 51.

Specifically, in the double structure container 40 filled with the first and second liquid concentrate compositions and the propellant, when the actuator 51 is not operated to be depressed, the first stem 44A and the second stem 44B are pushed upward to shut off their stem passages from the inside of the first pressure resistant container 41A and the second pressure resistant container 41B, respectively. On the other hand, when the actuator 51 is operated to be depressed, the first stem 44A and the second stem 44B are pressed down, and thereby their stem passages are simultaneously communicated with the inside of the first pressure resistant container 41A and of the second pressure resistant container 41B, respectively. As a result, the first liquid concentrate composition inside the first inner bag 45A in the first pressure resistant container 41A and the second liquid concentrate composition inside the second inner bag 45B in the second pressure resistant container 41B are discharged simultaneously. The first and second liquid concentrate compositions thus discharged simultaneously flows respectively through the stem passages in the first and second stems 44A and 44B and the first and second actuator passages 52A and 52B, and reach the discharge space 53. In the process of passing through the discharge space 53, the first and second liquid concentrate compositions are discharged from the discharge port 54 without being mixed with each other. Then the first liquid concentrate composition and the second liquid concentrate composition discharged from the discharge port 54 are mixed with each other by, for example, fingers of a user, at the application site to form a warming cream composition.

Figure 6:
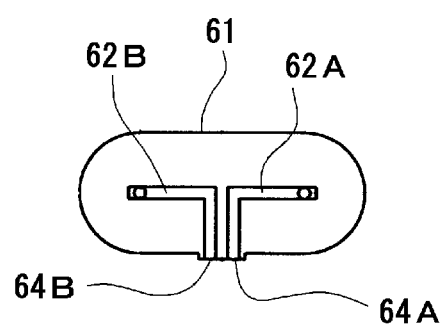
FIG. 6 is an illustration of yet another example of a configuration of a double structure container used in an aerosol product for forming a warming cream composition of the present invention.

FIG. 6 is an illustration of yet another example of a configuration of a double structure container used in an aerosol product for forming a warming cream composition of the present invention. Specifically, FIG. 6 is a sectional view for illustrating the configuration of the actuator for the double structure container.

This double structure container has the same configuration as that of the double structure container 40 shown in FIGS. 4 and 5 except that it is provided with an actuator 61 instead of the actuator 51 of the double structure container 40 of FIGS. 4 and 5. The actuator 61 has two discharge ports (specifically, a first discharge port 64A and a second discharge port 64B) from which the first and second liquid concentrate compositions are discharged separately from the two respective discharge ports.

That is to say, the double structure container of FIG. 6 includes the actuator 61, and a container main body having a similar configuration to that of the container main body shown in FIGS. 4 and 5 including the first pressure resistant container 41A, the second pressure resistant container 41B, and the container fixing member 48 constituting the double structure container 40.

The actuator 61 is configured to include a first actuator passage 62A that communicates with the stem passage of the first stem at one end and forms the first discharge port 64A at the other end, and a second actuator passage 62B that communicates with the stem passage of the second stem at one end and forms the second discharge port 64B at the other end.

The actuator 61 is shared by both of the first and second stems and provided on the upper ends of the first and second stems, similarly to the actuator 51 of the double structure container 40 shown in FIG. 4 and FIG. 5.

In the double structure container having such a configuration, when the actuator 61 is operated to be depressed in a state where the first and second liquid concentrate compositions and the propellant are filled therein, the first and second liquid concentrate compositions are discharged simultaneously from the first and second inner bags inside the first and second pressure resistant containers, respectively. Then, the first liquid concentrate composition is discharged from the first discharge port 64A through the stem passage in the first stem of the first aerosol valve and the first actuator passage 62A. On the other hand, the second liquid concentrate composition is discharged from the second discharge port 64B through the stem passage in the second stem of the second aerosol valve and the second actuator passage 62B. The first liquid concentrate composition discharged from the first discharge port 64A and the second liquid concentrate composition discharged from the second discharge port 64B are then mixed with each other by, for example, fingers of a user, to form a warming cream composition at the application site.

With the double structure container having the configuration mentioned above, the first liquid concentrate composition filled in the first liquid concentrate filling space and the second liquid concentrate composition filled in the second liquid concentrate filling space can be discharged simultaneously by the discharging mechanism. Furthermore, the amount of the first liquid concentrate composition discharged from the first liquid concentrate filling space and the amount of the second liquid concentrate composition discharged from the second liquid concentrate filling space can be adjusted at an appropriate amount ratio, specifically, in substantially the same amount.

In the aerosol product for forming a warming cream composition of the present invention, it is preferable that the mixture ratio of the first liquid concentrate composition discharged from the first liquid concentrate filling space and the second liquid concentrate composition discharged from the second liquid concentrate filling space (mass of the first liquid concentrate composition:mass of the second liquid concentrate composition) is 0.8:1.2 to 1.2:0.8.

That is to say, it is preferable that each of the discharge amount of the first liquid concentrate composition discharged from the first liquid concentrate filling space and the amount of the second liquid concentrate composition discharged from the second liquid concentrate filling space fits within a range of ±20% with respect to the average value of the discharge amounts of the first liquid concentrate composition and the second liquid concentrate composition.

Herein, when the mixture ratio (mass of the first liquid concentrate composition:mass of the second liquid concentrate composition) can be adjusted to fit within the range mentioned above by setting, for example, the viscosity of the first liquid concentrate composition at a temperature of 20° C. at 1000 to 125000 mPa·s, and the viscosity of the second liquid concentrate composition at a temperature of 20° C. at 1000 to 125000 mPa·s. Furthermore, preferably, with regards to the relation between the viscosity of the first liquid concentrate composition and the viscosity of the second liquid concentrate composition, the viscosity of the first liquid concentrate composition is made to be lower than the viscosity of the second liquid concentrate composition. That is to say, the viscosity of the second liquid concentrate composition is made to be higher than the viscosity of the first liquid concentrate composition.

When the mixture ratio (mass of the first liquid concentrate composition:mass of the second liquid concentrate composition) does not fit in the range mentioned above, a large difference occurs between the amount of the first liquid concentrate composition discharged from the first liquid concentrate filling space and the amount of the second liquid concentrate composition discharged from the second liquid concentrate filling space. As a result, the warming cream composition formed by mixing the first and second liquid concentrate compositions with each other may not exhibit a sufficient warming effect.

The aerosol product for forming a warming cream composition of the present invention described above is produced by filling the first liquid concentrate filling space within the double structure container with the first liquid concentrate composition, and the second liquid concentrate filling space with the second liquid concentrate composition, respectively, and filling the propellant filling space with the propellant.

The aerosol product for forming a warming cream composition of the present invention includes a double structure container having a discharging mechanism for simultaneously discharging the contents filled in the two liquid concentrate filling spaces. Furthermore, one of the two liquid concentrate filling spaces is filled with the first liquid concentrate composition having a specific viscosity, which is obtained by dispersing hydration exothermic substance powder in a specific ratio in a liquid medium containing a specific rate of higher alcohol and having a specific viscosity, while the other liquid concentrate filling space is filled with the second liquid concentrate composition containing a viscosity modifier in a specific ratio. Accordingly, in the first liquid concentrate composition, the hydration exothermic substance powder is always homogeneously dispersed in the liquid medium, and the liquid medium has miscibility to water. Therefore, when the first liquid concentrate composition is mixed with the second liquid concentrate composition, the homogeneously existing hydration exothermic substance powder evenly exhibits an appropriate exothermic effect. Furthermore, the first liquid concentrate composition and the second liquid concentrate composition can be simultaneously discharged in an appropriate amount (specifically, in the same discharge amount) from each of the liquid concentrate filling spaces in the double structure container. Therefore, the first liquid concentrate composition and the second liquid concentrate composition can always be mixed in a constant amount ratio, so that one liquid concentrate composition is not discharged excessively relative to the discharge amount of the other liquid concentrate composition. Furthermore, since a propellant is not discharged from the double structure container along with the first and second liquid concentrate compositions, no cooling sensation due to vaporization of the propellant occurs at the application site. As a result, a simple operation of the discharging mechanism, specifically, for example, only an operation of pressing down the actuator once (one push), allows the first and second liquid concentrate compositions to be discharged, and thereby a warming cream composition having a favorable warming effect can be always readily formed easily.

Therefore, the aerosol product for forming a warming cream composition of the present invention makes it possible to achieve dispersion stability of the hydration exothermic substance powder, and to easily form a warming cream composition having a sufficient warming effect.

Furthermore, in the aerosol product for forming a warming cream composition of the present invention, an incombustible compressed gas is used as the propellant for the first and second liquid concentrate compositions. Accordingly, the product can be used highly safely regardless of an environment in which it is used, and there is no risk of explosion when disposing of the double structure container.

Moreover, neither the first liquid concentrate composition nor the second liquid concentrate composition is exposed to the air outside the container. Therefore, absorption of moisture by the hydration exothermic substance, which generally has high moisture absorption property, is prevented, and unexpected exothermic effects do not occur. Therefore, long-term storage stability can be achieved.

Furthermore, the aerosol product for forming a warming cream composition of the present invention makes it possible to enjoy the formation process of the warming cream composition which consists of mixing the first liquid concentrate composition and the second liquid concentrate composition with each other, the change of the state of the mixture of the first liquid concentrate composition and the second liquid concentrate composition at the application site or the like, even when any one of the actuators shown in FIGS. 2, 3, 5, and 6 is used.

Such an aerosol product for forming a warming cream composition of the present invention can be used for a variety of purposes. It can be particularly suitably used for the human body, since a very favorable warming effect can be exhibited when it is applied to the human body.

Specifically, the aerosol product can be used for cosmetics such as cosmetic cream, pack agents and foundations, and toiletry products such as shaving cream and facial cleansers.

EXAMPLES

Hereinafter, Examples of the present invention will be described, but the present invention is not limited by these examples.

Examples 1 to 15 and Comparative Examples 1 to 7

Preparation of First Liquid Concentrate Composition

Firstly, according to the prescription of Tables 1 and 2, components other than hydration exothermic substance (zeolite) powder were warmed to 70° C., and mixed with each other. The mixture was cooled to room temperature while being stirred so as to produce a liquid media.

In each of the resultant liquid media, a viscosity at a temperature of 20° C. was measured using a BM rotary viscometer. Results are shown in Tables 1 and 2.

Next, hydration exothermic substance (zeolite) powder was blended to each of the resultant liquid media according to the prescription of Tables 1 and 2, and was homogeneously dispersed. Thus, the first liquid concentrate compositions were prepared.

For each of the resultant first liquid concentrate compositions, viscosity at a temperature of 20° C. was measured using a BM rotary viscometer. Results are shown in Tables 1 and 2.

Herein, the average particle diameter of the zeolite powder used as the hydration exothermic substance powder for the preparation of the first liquid concentrate composition was 11 μm.

Preparation of Second Liquid Concentrate Composition

According to the prescription of Table 3, a carboxyvinyl polymer (a viscosity modifier) was added and dispersed to purified water (water) while being stirred, and then a triethanolamine (a neutralizer) was added thereto. Thus, eight types of the second liquid concentrate compositions (hereinafter, also referred to as "composition (1)" to "composition (8)") were prepared.

For each of the resultant second liquid concentrate compositions, viscosity at a temperature of 20° C. was measured using a BM rotary viscometer. Results are shown in Table 3.

Production of Aerosol Product

A double structure container having the configuration shown in FIGS. 1 and 3 was prepared. According to the prescription of Tables 1 and 2, the first liquid concentrate filling space (first inner bag) of the double structure container was filled with the first liquid concentrate composition, while the second liquid concentrate filling space (second inner bag) was filled with the second liquid concentrate composition, and the propellant filling space was filled with nitrogen gas as the propellant so that the pressure in the product in the double structure container was 0.7 MPa at 25° C. Thus, the aerosol products were produced.

<Evaluation Test>

The aerosol products produced in the above-mentioned Examples 1 to 15 and Comparative Examples 1 to 7 were evaluated by the following method in terms of dispersion stability of the hydration exothermic substance powder, exothermic property of the discharged product and simultaneous discharge property. Results are shown in Tables 1 and 2.

(Evaluation of Dispersion Stability of Hydration Exothermic Substance Powder)

Each of the first liquid concentrate compositions in the same amount as that filled in the first liquid concentrate filling space of the aerosol product was enclosed in a hermetically sealed transparent container, allowed to stand in an environment having a temperature of 45° C. for one week, and the presence or absence of precipitation of the hydration exothermic substance (zeolite) powder was assessed by visual observation. Then, when no precipitation of the hydration exothermic substance powder was observed, the dispersion stability of the hydration exothermic substance powder was evaluated as "A" for having sufficient dispersion stability, and when the precipitation of the hydration exothermic substance powder was observed, the dispersion stability of the hydration exothermic substance powder was evaluated as "B" for being insufficient in the dispersion stability.

(Evaluation of Exothermic Property of Discharged Product)

Five grams of the content of each of the aerosol products was sprayed into a 50 ml glass beaker. The temperature (t0 [° C.]) of the discharged product in the beaker was measured, and the discharged product was stirred by slowly rotating a glass rod a total of ten times for one minute. Thereafter, the temperature (t [° C.]) of the discharged product in the glass beaker was measured. Then, the increased temperature (t−t0) [° C.] was calculated. When the increased temperature was 20° C. or more, the discharged product was evaluated as "A" for having a very good exothermic property; when the increased temperature was 15° C. or more and less than 20° C., the discharged product was evaluated as "B" for having a good exothermic property; when the increased temperature was 10° C. or more and less than 15° C., the discharged product was evaluated as "C" for having a sufficient exothermic property; and when the increased temperature was less than 10° C., the discharged product was evaluated as "D" for having an insufficient exothermic property.

(Evaluation of Simultaneous Discharge Property)

Two 50 ml beakers were prepared, and each of the aerosol products was sprayed. The composition discharged from the first liquid concentrate filling space was collected in one of the beakers, and the composition discharged from the second liquid concentrate filling space was collected in the other beaker. Then, a mass of the composition discharged from the first liquid concentrate filling space and a mass of the composition discharged from the second liquid concentrate filling space were measured, and the mass ratio of these masses was calculated. When the mass ratio (mass of the composition discharged from the first liquid concentrate filling space:mass of the composition discharged from the second liquid concentrate filling space) was 0.8:1.2 to 1.2:0.8, the simultaneous discharge property was evaluated as "A" for having a very good simultaneous discharge property; when the mass ratio (mass of the composition discharged from the first liquid concentrate filling space:mass of the composition discharged from the second liquid concentrate filling space) was 0.7:1.3 to 1.3:0.7, the simultaneous discharge property was evaluated as "B" for obtaining a sufficient simultaneous discharge property; and when the mass ratio (mass of the composition discharged from the first liquid concentrate filling space:mass of the composition discharged from the second liquid concentrate filling space) was out of the range corresponding to the evaluation "B," the simultaneous discharge property was evaluated as "C" for being insufficient in the simultaneous discharge property.

TABLE 1

| | | | | | Example 1 | Example 2 | Example 3 | Example 4 | Example 5 |
|---|---|---|---|---|---|---|---|---|---|
| Composition | First liquid concentrate composition | Liquid medium | Polyhydric alcohol (% by mass) | Polyethylene glycol | 67.000 | 65.000 | — | — | — |
| | | | | Glycerine | — | — | 69.800 | 69.700 | 69.510 |
| | | | | 1,3-butylene glycol | — | — | — | — | — |
| | | | Higher alcohol (% by mass) | Cetyl alcohol | 2.250 | 3.750 | 0.050 | 0.070 | 0.110 |
| | | | Anionic surfactant (% by mass) | Sodium cetylsulfate | 0.260 | 0.435 | 0.050 | 0.080 | 0.130 |
| | | | Esters (% by mass) | Isopropyl palmitate | 0.300 | 0.500 | 0.060 | 0.090 | 0.150 |
| | | | Wax (% by mass) | Beeswax | 0.190 | 0.315 | 0.040 | 0.060 | 0.100 |
| | | Hydration exothermic substance powder (% by mass) | Zeolite | | 30.000 | 30.000 | 30.000 | 30.000 | 30.000 |
| | | Total (% by mass) | | | 100.000 | 100.000 | 100.000 | 100.000 | 100.000 |
| | | Viscosity of liquid medium (mPa·s) | | | 1550 ※1 | 1750 ※1 | 1038 ※1 | 1360 ※1 | 1525 ※1 |
| | | Viscosity of first liquid concentrate composition (mPa·s) | | | 17500 ※2 | 30000 ※2 | 14000 ※2 | 19300 ※2 | 32750 ※2 |
| | Second liquid concentrate composition | Composition No. | | | Composition (1) | Composition (2) | Composition (3) | Composition (1) | Composition (2) |
| Evaluation Test | | Dispersion stability of hydration exothermic substance powder | | | A | A | A | A | A |
| | | Exothermic property of discharged product | | | B | B | C | C | C |
| | | Simultaneous discharge property | | | A | A | A | A | A |

| | | | | | Example 6 | Example 7 | Example 8 | Example 9 | Example 10 |
|---|---|---|---|---|---|---|---|---|---|
| Composition | First liquid concentrate composition | Liquid medium | Polyhydric alcohol (% by mass) | Polyethylene glycol | — | — | 82.000 | — | 87.000 |
| | | | | Glycerine | — | — | — | — | — |
| | | | | 1,3-butylene glycol | 67.000 | 65.000 | — | 57.000 | — |
| | | | Higher alcohol (% by mass) | Cetyl alcohol | 2.250 | 3.750 | 6.000 | 2.250 | 2.250 |
| | | | Anionic surfactant (% by mass) | Sodium cetylsulfate | 0.260 | 0.435 | 0.700 | 0.260 | 0.260 |
| | | | Esters (% by mass) | Isopropyl palmitate | 0.300 | 0.500 | 0.800 | 0.300 | 0.300 |
| | | | Wax (% by mass) | Beeswax | 0.190 | 0.315 | 0.500 | 0.190 | 0.190 |
| | | Hydration exothermic substance powder (% by mass) | Zeolite | | 30.000 | 30.000 | 10.000 | 40.000 | 10.000 |
| | | Total (% by mass) | | | 100.000 | 100.000 | 100.000 | 100.000 | 100.000 |
| | | Viscosity of liquid medium (mPa·s) | | | 1200 ※1 | 4050 ※1 | 3300 ※1 | 2340 ※1 | 1150 ※1 |
| | | Viscosity of first liquid concentrate composition (mPa·s) | | | 3150 ※1 | 8300 ※1 | 3550 ※1 | 17000 ※2 | 1200 ※1 |
| | Second liquid concentrate composition | Composition No. | | | Composition (5) | Composition (4) | Composition (5) | Composition (1) | Composition (6) |
| Evaluation Test | | Dispersion stability of hydration exothermic substance powder | | | A | A | A | A | A |
| | | Exothermic property of discharged product | | | C | C | C | B | C |
| | | Simultaneous discharge property | | | A | A | A | A | A |

TABLE 1-continued

|  |  |  |  |  | Example 11 | Example 12 | Example 13 | Example 14 | Example 15 |
|---|---|---|---|---|---|---|---|---|---|
| Composition | First liquid concentrate composition | Liquid medium | Polyhydric alcohol (% by mass) | Polyethylene glycol | 77.000 | 83.000 | 62.000 | 60.000 | — |
|  |  |  |  | Glycerine | — | — | — | — | 69.410 |
|  |  |  |  | 1,3-butylene glycol | — | — | — | — | — |
|  |  | Higher alcohol (% by mass) | | Cetyl alcohol | 2.250 | 5.250 | 6.000 | 7.500 | 0.140 |
|  |  | Anionic surfactant (% by mass) | | Sodium cetylsulfate | 0.260 | 0.610 | 0.700 | 0.870 | 0.160 |
|  |  | Esters (% by mass) | | Isopropyl palmitate | 0.300 | 0.700 | 0.800 | 1.000 | 0.180 |
|  |  | Wax (% by mass) | | Beeswax | 0.190 | 0.440 | 0.500 | 0.630 | 0.110 |
|  |  | Hydration exothermic substance powder (% by mass) | | Zeolite | 20.000 | 10.000 | 30.000 | 30.000 | 30.000 |
|  |  | Total (% by mass) | | | 100.000 | 100.000 | 100.000 | 100.000 | 100.000 |
|  |  | Viscosity of liquid medium (mPa·s) | | | 1300 ※1 | 1850 ※1 | 5300 ※1 | 6900 ※1 | 1625 ※1 |
|  |  | Viscosity of first liquid concentrate composition (mPa·s) | | | 1600 ※1 | 2650 ※1 | 59500 ※2 | 93500 ※2 | 64000 ※2 |
|  | Second liquid concentrate composition | Composition No. | | | Composition (6) | Composition (5) | Composition (8) | Composition (8) | Composition (8) |
| Evaluation Test | | Dispersion stability of hydration exothermic substance powder | | | A | A | A | A | A |
|  | | Exothermic property of discharged product | | | B | C | B | B | C |
|  | | Simultaneous discharge property | | | A | A | B | B | B |

*: Average molecular weight of polyethylene glycol: 400
*1: Method for measuring viscosity: BM rotary viscometer, rotor No. 4, 60 rpm
*2: Method for measuring viscosity: BM rotary viscometer, rotor No. 4, 12 rpm

TABLE 2

|  |  |  |  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|---|---|
| Composition | First liquid concentrate composition | Liquid medium | Polyhydric alcohol (% by mass) | Polyethylene glycol | 69.000 | 68.000 | — | — | — | — | — |
|  |  |  |  | Glycerine | — | — | — | — | — | — | — |
|  |  |  |  | 1,3-butylene glycol | — | — | 69.000 | 68.000 | 62.000 | 87.000 | 77.000 |
|  |  | Higher alcohol (% by mass) | | Cetyl alcohol | 0.750 | 1.500 | 0.750 | 1.500 | 6.000 | 2.250 | 2.250 |
|  |  | Anionic surfactant (% by mass) | | Sodium cetylsulfate | 0.090 | 0.170 | 0.090 | 0.170 | 0.700 | 0.260 | 0.260 |
|  |  | Esters (% by mass) | | Isopropyl palmitate | 0.100 | 0.200 | 0.100 | 0.200 | 0.800 | 0.300 | 0.300 |
|  |  | Wax (% by mass) | | Beeswax | 0.060 | 0.130 | 0.060 | 0.130 | 0.500 | 0.190 | 0.190 |
|  |  | Hydration exothermic substance powder (% by mass) | | Zeolite | 30.000 | 30.000 | 30.000 | 30.000 | 5330.000 | 10.000 | 20.000 |
|  |  | Total (% by mass) | | | 100.000 | 100.000 | 100.000 | 100.000 | 100.000 | 100.000 | 100.000 |
|  |  | Viscosity of liquid medium (mPa·s) | | | 200 ※1 | 750 ※1 | 100 ※1 | 450 ※1 | 10400 ※2 | 800 ※1 | 900 ※1 |
|  |  | Viscosity of first liquid concentrate composition (mPa·s) | | | 850 ※1 | 2750 ※1 | 450 ※1 | 1100 ※1 | 100000 ※2 | 850 ※1 | 1050 ※1 |

TABLE 2-continued

|  |  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|
| Second liquid concentrate composition | Composition No. | Composition (6) | Composition (6) | Composition (7) | Composition (6) | Composition (8) | Composition (6) | Composition (6) |
| Evaluation Test | Dispersion stability of hydration exothermic substance powder | B | B | B | B | A | B | B |
|  | Exothermic property of discharged product | B | B | C | C | C | D | C |
|  | Simultaneous discharge property | A | A | A | A | C | A | A |

*: Average molecular weight of polyethylene glycol: 400
*1: Method for measuring viscosity: BM rotary viscometer, rotor No. 4, 60 rpm
*2: Method for measuring viscosity: BM rotary viscometer, rotor No. 4, 6 rpm

TABLE 3

|  |  |  | Composition 1 | Composition 2 | Composition 3 | Composition 4 | Composition 5 | Composition 6 | Composition 7 | Composition 8 |
|---|---|---|---|---|---|---|---|---|---|---|
| Second liquid concentrate composition | Solvent | Purified water (% by mass) | 98.00 | 97.50 | 98.40 | 99.20 | 99.60 | 99.80 | 99.90 | 97.00 |
|  | Viscosity modifier | Carboxyvinyl polymer (% by mass) | 1.00 | 1.25 | 0.80 | 0.40 | 0.20 | 0.10 | 0.05 | 1.50 |
|  | Neutralizer | Triethanolamine (% by mass) | 1.00 | 1.25 | 0.80 | 0.40 | 0.20 | 0.10 | 0.05 | 1.50 |
|  |  | Total (% by mass) | 100.00 | 100.00 | 100.00 | 100.00 | 100.00 | 100.00 | 100.00 | 100.00 |
|  |  | Viscosity of second liquid concentrate composition (mPa·s) | 100000 ※3 | 125000 ※4 | 77000 ※3 | 32000 ※2 | 18000 ※2 | 8000 ※1 | 4000 ※1 | 130000 ※4 |

*: Average molecular weight of polyethylene glycol: 400
*1: Method for measuring viscosity: BM rotary viscometer, rotor No. 4, 30 rpm
*2: Method for measuring viscosity: BM rotary viscometer, rotor No. 4, 12 rpm
*3: Method for measuring viscosity: BM rotary viscometer, rotor No. 4, 6 rpm
*4: Method for measuring viscosity: BM rotary viscometer, rotor No. 6, 2 rpm It is confirmed from the results of Table 1 that the aerosol products of Examples 1 to 15 achieved dispersion stability of the hydration exothermic substance powder, that the first liquid concentrate composition and the second liquid concentrate composition were discharged in substantially the same amount, and that a warming cream composition having a sufficient warming effect could be easily formed. In particular, it is demonstrated that the aerosol products of Examples 1 to 12 achieved excellent simultaneous discharge property, since the viscosity (at 20° C.) of the first liquid concentrate composition and the second liquid concentrate composition fell in the range from 1000 to 125000 mPa·s.

On the other hand, from the results of Tables 2 and 3, in the aerosol product of Comparative Examples 1 to 4 and 7, due to the viscosity of the liquid medium constituting the first liquid concentrate composition being too low, dispersion stability of the hydration exothermic substance powder in the first liquid concentrate composition was not achieved. Furthermore, with regard to the aerosol product according to Comparative Example 5, due to the viscosity of the second liquid concentrate composition being too high, a large difference occurred between the discharge amount of the first liquid concentrate composition and the discharge amount of the second liquid concentrate composition. Furthermore, in the aerosol product according to Comparative Example 6, due to the viscosity of the liquid medium constituting the first liquid concentrate composition and the viscosity of the first liquid concentrate composition being too low, dispersion stability of the hydration exothermic substance powder in the first liquid concentrate composition was not achieved. Moreover, no sufficient exothermic property was achieved in the discharged product.

Furthermore, it was demonstrated that, with regard to the aerosol products according to Examples 1 to 15, the resultant warming cream compositions provided a favorable sense of use free from sticky or frictional feelings occurring after use.

Furthermore, it was demonstrated that, even after the aerosol product according to Examples 1 to 15 had been stored in an environment at a temperature of 45° C. for such a long time as one month, a sufficient warming cream composition was successfully formed.

REFERENCE SIGNS LIST 10 double structure container
11 pressure resistant container
12 aerosol valve
13A first housing
13B second housing
14A first stem
14B second stem
15A first inner bag
15B second inner bag
16A first dip tube
16B second dip tube 21 actuator
22A first actuator passage
22B second actuator passage
23 discharge space
24 discharge port
31 actuator
32A first actuator passage
32B second actuator passage
34A first discharge port
34B second discharge port
40 double structure container
41A first pressure resistant container
41B second pressure resistant container
42A first aerosol valve
42B second aerosol valve
43A first housing
43B second housing
44A first stem
44B second stem
45A first inner bag
45B second inner bag
48 container fixing member
51 actuator
52A first actuator passage
52B second actuator passage
53 discharge space
54 discharge port
61 actuator
62A first actuator passage
62B second actuator passage
64A first discharge port
64B second discharge port

The invention claimed is:

1. An aerosol product for forming a warming cream composition, comprising:
a double structure container including a propellant filling space, two independent liquid concentrate filling spaces, and a discharging mechanism for simultaneously discharging contents filled in the two liquid concentrate filling spaces,
wherein
the propellant filling space in the double structure container is filled with a propellant composed of compressed gas;
a first liquid concentrate filling space in the double structure container is filled with a first liquid concentrate composition, and a second liquid concentrate filling space in the double structure container is filled with a second liquid concentrate composition;
the first liquid concentrate composition includes hydration exothermic substance powder dispersed in a liquid medium containing a polyhydric alcohol and a higher alcohol with 16 or more carbon atoms, wherein the liquid medium has a viscosity of 1000 to 10000 mPa·s at a temperature of 20° C., a content of the hydration exothermic substance powder is 10 to 40% by mass, a content of the higher alcohol is 0.05 to 20% by mass, the first liquid concentrate composition has a viscosity of 1000 to 125000 mPa·s at a temperature of 20° C., the hydration exothermic substance powder comprises at least one of zeolite, calcium chloride, magnesium chloride, magnesium sulfate, sodium carbonate, and silicic anhydride, the first liquid concentrate composition comprises substantially no water, and the first liquid concentrate composition comprises 0.05 to 0.87% by mass of a surfactant selected from the group consisting of an anionic surfactant, a nonionic surfactant having a HLB value of 6 to 13, and mixtures thereof;
the second liquid concentrate composition contains water and a viscosity modifier, wherein a content of the water is 90 to 99.9% by mass, a content of the viscosity modifier is 0.1 to 10% by mass; and
the first liquid concentrate composition discharged from the first liquid concentrate filling space and the second liquid concentrate composition discharged from the second liquid concentrate filling space are mixed with each other to form a warming cream composition.

2. The aerosol product for forming a warming cream composition according to claim 1, wherein a mixture ratio of the first liquid concentrate composition discharged from the first liquid concentrate filling space and the second liquid concentrate composition discharged from the second liquid concentrate filling space, that is a ratio of mass of the first liquid concentrate composition to mass of the second liquid concentrate composition, is 0.8:1.2 to 1.2:0.8.

3. The aerosol product for forming a warming cream composition according to claim 1, wherein the second liquid concentrate composition has a viscosity of 4000 to 130000 mPa·s at a temperature of 20° C.

4. The aerosol product for forming a warming cream composition according to claim 3, wherein the second liquid concentrate composition has a viscosity of 10000 to 125000 mPa·s at a temperature of 20° C.

5. The aerosol product for forming a warming cream composition according to claim 1, wherein the product is used for a human body.

6. The aerosol product for forming a warming cream composition according to claim 1, wherein the hydration exothermic substance powder comprises zeolite.

7. The aerosol product for forming a warming cream composition according to claim 1, wherein the second liquid concentrate composition further comprises a neutralizer.

8. The aerosol product for forming a warming cream composition according to claim 1, wherein the surfactant is the anionic surfactant.

9. The aerosol product for forming a warming cream composition according to claim 1, wherein the content of the higher alcohol is 0.05 to 8% by mass.

10. The aerosol product for forming a warming cream composition according to claim 1, wherein warming cream composition has a content of the polyhydric alcohol is at least 57% by mass.

11. The aerosol product for forming a warming cream composition according to claim 1, a content of the viscosity modifier is 0.5 to 1.5% by mass.

* * * * *